US009510613B2

(12) United States Patent
Takamura et al.

(10) Patent No.: US 9,510,613 B2
(45) Date of Patent: *Dec. 6, 2016

(54) PANAXADIOL-CONTAINING COMPOSITION

(75) Inventors: Yusuke Takamura, Tokyo (JP);
Mitsuru Nomura, Tokyo (JP); Hideaki Iwasaki, Tokyo (JP)

(73) Assignee: LION CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/114,831

(22) PCT Filed: Apr. 16, 2012

(86) PCT No.: PCT/JP2012/060283
§ 371 (c)(1),
(2), (4) Date: Oct. 30, 2013

(87) PCT Pub. No.: WO2012/150675
PCT Pub. Date: Nov. 8, 2012

(65) Prior Publication Data
US 2014/0073617 A1    Mar. 13, 2014

(30) Foreign Application Priority Data

May 2, 2011    (JP) .................. 2011-103142

(51) Int. Cl.
A61K 47/24     (2006.01)
A61K 31/58     (2006.01)
A61K 47/26     (2006.01)
A23L 1/30      (2006.01)
A23L 1/035     (2006.01)
A61K 31/575    (2006.01)
A61K 31/685    (2006.01)
A61K 31/7012   (2006.01)
A61K 9/00      (2006.01)
A61K 9/107     (2006.01)
A23L 2/52      (2006.01)

(52) U.S. Cl.
CPC .............. A23L 1/3002 (2013.01); A23L 1/035 (2013.01); A23L 1/30 (2013.01); A23L 2/52 (2013.01); A23L 29/10 (2016.08); A23L 33/10 (2016.08); A23L 33/105 (2016.08); A61K 9/0095 (2013.01); A61K 9/107 (2013.01); A61K 31/575 (2013.01); A61K 31/58 (2013.01); A61K 31/685 (2013.01); A61K 31/7012 (2013.01); A61K 47/24 (2013.01); A61K 47/26 (2013.01)

(58) Field of Classification Search
USPC ........................................ 514/172
See application file for complete search history.

(56) References Cited

U.S. PATENT DOCUMENTS 4,338,342 A *   7/1982  Tan et al. ............... 426/308
2008/0038335 A1  2/2008  Huang
2012/0252768 A1* 10/2012  Iwasaki et al. ........... 514/170
2014/0050805 A1  2/2014  Kambayashi et al.

FOREIGN PATENT DOCUMENTS

| CN | 1109712 A | 10/1995 |
|---|---|---|
| CN | 1628677 A | 6/2005 |
| CN | 1706428 A | 12/2005 |
| CN | 101263908 A | 9/2008 |
| EP | 0659347 A1 | 6/1995 |
| EP | 0659347 * | 8/2001 |
| EP | 2698161 A1 | 2/2014 |
| JP | 2000-354476 A | 12/2000 |
| JP | 2003-81846 A | 3/2003 |
| JP | 2003-246724 A | 9/2003 |
| JP | 2006-104084 A | 4/2006 |
| JP | 2008-81473 A | 4/2008 |
| JP | 2008-101218 A | 5/2008 |
| JP | 2008-536879 A | 9/2008 |
| JP | 2011-026314 | 2/2011 |
| WO | WO 03/072085 A1 | 9/2003 |
| WO | WO 2011/002033 A1 | 1/2011 |

OTHER PUBLICATIONS

International Search Report (PCT/ISA/210) mailed on Jul. 3, 2012, by the Japanese Patent Office as the International Searching Authority for International Application No. PCT/JP2012/060283.
Written Opinion (PCT/ISA/237) mailed on Jul. 3, 2012, by the Japanese Patent Office as the International Searching Authority for International Application No. PCT/JP2012/060283.
Office Action issued in corresponding Chinese Application No. 201280021483.2 on Sep. 28, 2014 (9 pages).
Extended Search Report issued in corresponding European Application No. 12779418 on Oct. 6, 2014 (5 pages).
Office Action issued in corresponding Korean Application No. 10-2013-7029049 on Feb. 26, 2015 (9 pages).
Yim: "The Conversion of Ginsenoside by Microorganisms and Acid Hydrolysis," Hallym University, 2009.
Office Action issued by the Chinese Patent Office on May 18, 2015 in corresponding Chinese Patent Application No. 201280021483.2 (12 pages).
Vita Health Ginkgo Leaf Extract (Ball) 120 tablets, Jun. 13, 2010, [online] https://web.archive.org/web/20100613184400/http://www.kenko.com/product/item/itm_8847790072.html.

* cited by examiner

Primary Examiner — Shirley V Gembeh
(74) Attorney, Agent, or Firm — Buchanan, Ingersoll & Rooney PC

(57) ABSTRACT

A panaxadiol-containing composition, containing: panaxadiol; and at least one of sucrose fatty acid ester and lecithin.

2 Claims, 2 Drawing Sheets

PANAXADIOL-CONTAINING COMPOSITION

TECHNICAL FIELD

The present invention relates to a panaxadiol-containing composition.

BACKGROUND ART

Panaxadiol is an aglycon formed after the sugar moiety has been removed from saponin (glycoside) of plants, and has been known to have high safety, be capable of being ingested as food or beverage, and have excellent blood glucose level-controlling effects and glucose metabolism-improving effects (see PTL 1). The panaxadiol has higher absorption in vivo than that of saponin. However, for the purpose of sufficiently exerting the blood glucose level-controlling effects and the glucose metabolism-improving effects, there has been a need to provide a panaxadiol-containing composition which has further improved absorption in vivo of panaxadiol and achieves great effects in a smaller amount.

During a process of absorbing ingested matter in vivo, the ingested matter should be solubilized in a digestive tract which is hydrophilic, and then passed through a cell membrane which is hydrophobic. That is, a balance between hydrophilicity and hydrophobicity is important for absorbing ingested matter in vivo. The panaxadiol has high hydrophobicity, therefore, it is guessed that improvement of the high hydrophobicity of panaxadiol can further improve absorption in vivo of panaxadiol.

Therefore, at present, there is a need to provide a panaxadiol-containing composition which has improved absorption in vivo of panaxadiol.

CITATION LIST

Patent Literature

PTL 1: Japanese Patent Application Laid-Open (JP-A) No. 2011-26314

SUMMARY OF INVENTION

Technical Problem

The present invention aims to solve the above existing problems and achieve the following object. Specifically, an object of the present invention is to provide a panaxadiol-containing composition which has improved absorption in vivo of panaxadiol.

Solution to Problem

The present inventors conducted extensive studies to solve the above problems and have obtained the following finding. Specifically, they have found that a panaxadiol-containing composition which contains panaxadiol and at least one of sucrose fatty acid ester and lecithin can improve absorption in vivo of the panaxadiol. The present invention has been accomplished on the basis of this finding.

The present invention is based on the above finding obtained by the present inventors, and a means for solving the above problems is a panaxadiol-containing composition which contains panaxadiol and at least one of sucrose fatty acid ester and lecithin.

Advantageous Effects of Invention

The present invention can provide a panaxadiol-containing composition which has improved absorption in vivo of panaxadiol. These can solve the above existing problems and achieve the above object.

DESCRIPTION OF EMBODIMENTS (Panaxadiol-Containing Composition)

Figure 1:
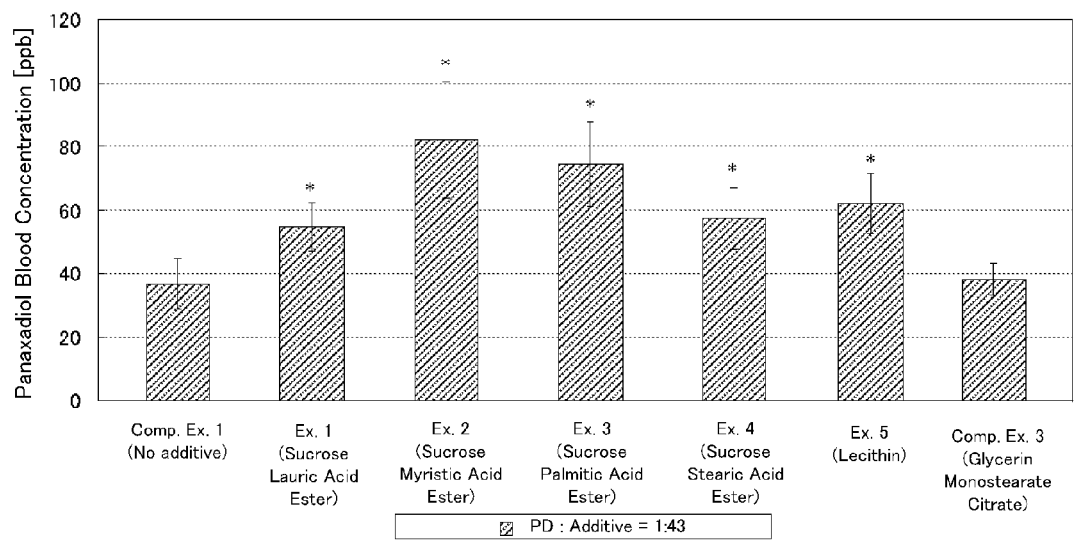
FIG. 1 shows results of panaxadiol concentrations in blood (PD blood concentrations; unit: ppb) of groups which ingested mixed feeds of Examples 1 to 5 and Comparative Examples 1 and 3.

A panaxadiol-containing composition of the present invention contains panaxadiol and at least one of sucrose fatty acid ester and lecithin; and, if necessary, further contains other ingredients.

<Panaxadiol>

Panaxadiol (PD) is a compound represented by the following Structural Formula (1) and belonging to dammarane-type triterpenes. The panaxadiol is an aglycon formed after the sugar moiety has been removed from saponin (glycoside) of plants and then the side chain has been ring-closed (hereinafter may be referred to as "sapogenin").

Structural Formula (1)

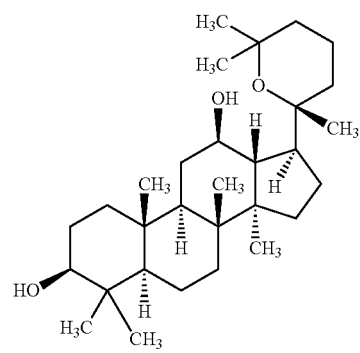

A method for obtaining the panaxadiol is not particularly limited and may be appropriately selected depending on the intended purpose. For example, the panaxadiol may be extracted from saponin-containing plants, synthesized, or a commercial product.

Of these, the panaxadiol is preferably extracted from saponin-containing plants because a panaxadiol-containing composition which has high safety can be obtained. The panaxadiol is more preferably obtained by subjecting a saponin-containing plant to an aqueous strong acid solution having a predetermined concentration to thereby hydrolyze saponin contained in the plant (herein may be referred to as "hydrolysis step"); neutralizing a liquid obtained after the hydrolysis (herein may be referred to as "neutralizing step"); filtrating the liquid obtained after the hydrolysis to thereby obtain a residue (herein may be referred to as "filtrating step"); and drying the residue (herein may be referred to as "drying step") from the viewpoint of easily producing the panaxadiol in high yield.

<<Saponin-Containing Plant>>

A saponin-containing plant used as a raw material of the panaxadiol is not particularly limited and may be appropriately selected depending on the intended purpose, as long as it is a natural product containing saponin. Examples of the saponin-containing plant include *Panax japonicus* (Araliaceae); *Bupleurum scorzonerifolium* (Apiaceae); *Polygala tenuifolia* (Polygalaceae); *Polygala senega* (Polygalaceae); *Platycodon grandillorum* (Campanulaceae); *Gynostemma pentaphyllum* (Cucurbitaceae); *Glycyrrhiza glabra* (Leguminosae); *Achyranthes bidentata* var. *fauriei* (Amaranthaceae); *Akebia trifoliate* (*Akebia*); *Ziziphus jujuba* (Rhamnaceae); *Anemarrhena asphodeloides* (Liliaceae); *Ophiopogon japonicus* (Liliaceae); and *Dioscorea tokoro* (Dioscoreaceae). These may be used alone or in combination.

Examples of the raw material include roots of *Panax notoginseng*, roots of *Panax ginseng*, roots of *Panax japonicus*, roots of *Eleutherococcus senticosus*, roots of *Aralia elata*, roots of *Aralia cordata*, roots of *Bupleurum scorzonerifolium*, roots of *Polygala tenuifolia*, roots of *Polygala senega*, roots of *Platycodon grandiflorum*, whole plants of *Gynostemma pentaphyllum*, roots of *Glycyrrhiza glabra*, roots of *Achyranthes bidentata* var. *fauriei*, stems of *Akebia trifoliate*, fruits of *Ziziphus jujuba*, rhizomes of *Anemarrhena asphodeloides*, roots of *Ophiopogon japonicus*, and rhizomes of *Dioscorea tokoro*.

Of these, roots of *Panax notoginseng* (Araliaceae), roots of *Panax ginseng* (Araliaceae), roots of *Panax japonicus* (Araliaceae), roots of *Eleutherococcus senticosus* (Araliaceae), roots of *Aralia elata* (Araliaceae), roots of *Aralia cordata* (Araliaceae), and whole plants of *Gynostemma pentaphyllum* (Cucurbitaceae) are preferred, and roots of *Panax notoginseng* (Araliaceae) is particularly preferred due to the highest yield of sapogenin.

The saponin-containing plant collected from nature may be used without pretreatment. However, by using the saponin-containing plant which has been subjected to pretreatment, hydrolysis described below can be more effectively performed. The pretreatment is performed by appropriately combining, for example, washing, drying, cutting, crushing, and pulverizing. In particular, the saponin-containing plant is preferably used in a pulverized powder form. Alternatively, the saponin-containing plant may be a commercial product.

<Hydrolysis Step>

The hydrolysis step is a step of subjecting the saponin-containing plant to an aqueous strong acid solution having a predetermined concentration to hydrolyze saponin contained in the plant, to thereby generate sapogenin which is superior in absorption in vivo to the saponin, i.e., panaxadiol.

The aqueous strong acid solution is not particularly limited, so long as it is an aqueous solution containing a strong acid, and may be appropriately selected depending on the intended purpose. The aqueous strong acid solution is preferably an aqueous solution containing an inorganic acid such as hydrochloric acid, phosphoric acid, sulfuric acid or nitric acid. These may be used alone or in combination of two or more thereof. Among them, an aqueous solution containing hydrochloric acid is more preferred.

The concentration of the acid in the aqueous strong acid solution is not particularly limited and may be appropriately selected depending on the intended purpose. It is preferably 0.01 mol/L to 4 mol/L, more preferably 0.5 mol/L to 3 mol/L. When the concentration of the acid in the aqueous strong acid solution is less than 0.01 mol/L, the hydrolysis is not sufficiently conducted and as a result the panaxadiol may not efficiently be obtained. Whereas when it is more than 4 mol/L, the hydrolysis may excessively proceed and there may be a disadvantage in terms of cost. When the concentration of the acid in the aqueous strong acid solution falls within the above preferred range, the hydrolysis is sufficiently conducted and as a result the panaxadiol can efficiently be obtained.

The amount of the aqueous strong acid solution used is not particularly limited and may be appropriately selected depending on the intended purpose. It is preferably 2 times by volume to 20 times by volume relative to the saponin-containing plant. When the amount of the aqueous strong acid solution used is less than 2 times by volume relative to the saponin-containing plant, the saponin-containing plant is not sufficiently immersed in the aqueous strong acid solution and as a result the hydrolysis cannot sufficiently be conducted. Whereas when it is more than 20 times by volume, there may be a disadvantage in terms of cost since the reaction is saturated.

—Lower Alcohol—

The hydrolysis is preferably performed in the presence of a lower alcohol. Use of the lower alcohol in the hydrolyzing step can improve the affinity between the saponin-containing plant and the aqueous strong acid solution, to thereby allow the hydrolysis to proceed efficiently.

Also, use of the lower alcohol is advantageous in that the lower alcohol can improve the taste and handling of the obtained panaxadiol.

The lower alcohol is not particularly limited and may be appropriately selected depending on the intended purpose. Examples thereof include alcohols having 1 to 5 carbon atoms. These may be used alone or in combination of two or more thereof. Among them, methanol, ethanol and propanol are preferred, with ethanol being preferred in terms of safety.

The amount of the lower alcohol used is not particularly limited and may be appropriately selected depending on the intended purpose. It is preferably 1% by volume to 80% by volume, more preferably 10% volume to 50% by volume, particularly preferably 20% by volume to 40% by volume, relative to the total amount of the hydrolyzation liquid. When the amount of the lower alcohol used is less than 1% by volume relative to the total amount of the hydrolyzation liquid, the panaxadiol may not efficiently be obtained. Whereas when it is more than 80% by volume, the panaxadiol cannot efficiently be obtained and there may be a disadvantage in terms of cost. When the amount of the lower alcohol used falls within the above preferred range, the panaxadiol can efficiently be obtained, which is advantageous.

Notably, the "total amount of the hydrolyzation liquid" refers to the total amount of the reaction liquid containing the aqueous strong acid solution and the lower alcohol.

The total amount of the reaction liquid containing the aqueous strong acid solution and the lower alcohol (the total amount of the hydrolyzation liquid) is preferably 2 times by volume to 20 times by volume relative to the saponin-containing plant. When the total amount of the reaction liquid is less than 2 times by volume relative to the saponin-containing plant, the saponin-containing plant is not sufficiently immersed in the reaction liquid and as a result the hydrolysis cannot sufficiently be conducted. Whereas when it is more than 20 times by volume, there may be a disadvantage in terms of cost since the reaction is saturated.

The temperature at which the hydrolysis is conducted is not particularly limited and may be appropriately selected depending on the intended purpose. It is preferably 60° C. to 100° C., more preferably 70° C. to 90° C. When the temperature at which the hydrolysis is conducted is less than 60° C., the hydrolysis is not sufficiently conducted and as a result the panaxadiol may not efficiently be obtained. Whereas when it is more than 100° C., it is necessary to use special production facilities and as a result there may be a disadvantage in terms of cost. When the temperature at which the hydrolysis is conducted falls within the above more preferred range, the acid-treated product can efficiently be obtained and also the panaxadiol can efficiently be obtained, which is advantageous.

The time for which the hydrolysis is conducted is not particularly limited and may be appropriately selected depending on the intended purpose. It is preferably 30 min to 24 hours, more preferably 2 hours to 8 hours. When the time for which the hydrolysis is conducted is shorter than 30 min, the hydrolysis is not sufficiently conducted and as a result the panaxadiol may not efficiently be obtained. Whereas it is longer than 24 hours, the reaction may excessively proceed and there may be a disadvantage in terms of cost. When the time for which the hydrolysis is conducted falls within the above more preferred range, the panaxadiol can efficiently be obtained, which is advantageous.

<<Neutralizing Step>>

The neutralizing step is a step of neutralizing the liquid hydrolyzed in the hydrolyzing step.

The method for the neutralization is not particularly limited and may be appropriately selected from known methods depending on the intended purpose. Examples thereof include a method in which an aqueous solution of a strong base such as sodium hydroxide or potassium hydroxide is appropriately added to the hydrolyzed liquid after the hydrolysis.

The pH of the liquid after the neutralization is preferably 5 to 8, more preferably neutral.

<<Filtrating Step>>

The filtrating step is a step of filtrating the hydrolyzed liquid obtained after the neutralization in the neutralizing step, to thereby be separated into a filtrate and a residue.

The method for the filtration is not particularly limited and may be appropriately selected from known methods depending on the intended purpose. Notably, after the filtration, washing with water may be repeated until the salts are completely removed.

—Water-Added Filtration—

When the lower alcohol is not used in the hydrolyzing step, the liquid obtained after the neutralization can be subjected to the filtration without any further treatment. However, when the lower alcohol is used in the hydrolyzing step, prior to the filtration, the concentration of the lower alcohol in the liquid obtained after the hydrolysis is preferably reduced with the addition of water, for the purpose of making the panaxadiol remain in the residue.

In this case, although the amount of water to be added is preferably more, the concentration of the lower alcohol in the liquid obtained after the hydrolysis is preferably less. Specifically, water is added so that the concentration of the lower alcohol in the liquid obtained after the hydrolysis is preferably 50% by volume or less, more preferably 30% by volume or less, particularly preferably 10% by volume or less. When the concentration of the lower alcohol in the liquid obtained after the hydrolysis is higher than 50% by volume upon the filtration, the panaxadiol dissolves in the lower alcohol and is removed as the filtrate, so that the amount of sapogenins in the residue may decrease disadvantageously. When the concentration of the lower alcohol in the liquid obtained after the hydrolysis falls within the above particularly preferred range, it is possible to further increase the amount of the panaxadiol contained in the residue, which is advantageous.

—Filtration After Vacuum Concentration—

Prior to the filtration, the concentration of the lower alcohol in the liquid obtained after the hydrolysis is preferably reduced with distillation by vacuum concentration, for the purpose of making the panaxadiol remain in the residue.

In this case, the temperature for the vacuum concentration is not particularly limited and may be appropriately selected depending on the intended purpose, but is preferably 70° C. or lower, more preferably 40° C. to 50° C.

The concentration of the lower alcohol is not particularly limited and may be appropriately selected depending on the intended purpose. However, the lower alcohol is preferably distilled off so as to have the concentration of 50% by volume or less, more preferably 30% by volume or less, particularly preferably 10% by volume or less. When the concentration of the lower alcohol in the liquid obtained after the hydrolysis is higher than 50% by volume upon the filtration, the panaxadiol dissolves in the lower alcohol and is removed as the filtrate, so that the amount of the panaxadiol in the residue may decrease disadvantageously. When the concentration of the lower alcohol in the liquid obtained after the hydrolysis falls within the above particularly preferred range, it is possible to further increase the amount of the panaxadiol contained in the residue, which is advantageous.

The vacuum concentration and the water-added filtration may be performed alone, or as a series of steps. When the vacuum concentration and the water-added filtration are performed as a series of steps, water is added to the liquid obtained after the vacuum concentration, so as to perform the water-added filtration.

<<Drying Step>>

The drying step is a step of drying the residue after the filtrating step to obtain a dry product of the panaxadiol.

The method for the drying is not particularly limited and may be appropriately selected from known methods depending on the intended purpose. Examples thereof include freeze drying, air-circulation drying, reduced-pressure drying and heating drying.

The panaxadiol obtained by subjecting the saponin-containing plant to the aqueous strong acid solution to hydrolyze saponin contained in the plant may be used in a dried powder form, or in a solution form which is obtained by suspending the panaxadiol in a solvent such as water or ethanol to thereby dilute to a desired concentration. However, the panaxadiol is preferably used in the powder form from the viewpoint of easily producing the panaxadiol-containing composition.

The amount of the panaxadiol in the panaxadiol-containing composition is not particularly limited and may be appropriately selected depending on the intended purpose.

<Sucrose Fatty Acid Ester and/or Lecithin>

<<Sucrose Fatty Acid Ester>>

A method for obtaining the sucrose fatty acid ester is not particularly limited and may be appropriately selected depending on the intended purpose. For example, the sucrose fatty acid ester may be synthesized, or a commercial product.

A method for synthesizing the sucrose fatty acid ester is not particularly limited and may be appropriately selected depending on the intended purpose. For example, the sucrose fatty acid ester can be synthesized by esterifying sucrose with a fatty acid.

The number of carbon atoms in the fatty acid is not particularly limited and may be appropriately selected depending on the intended purpose, but is preferably 10 to 20, more preferably 12 to 18, particularly preferably 14 to 16.

The type of the sucrose fatty acid ester is not particularly limited and may be appropriately selected depending on the intended purpose. Examples thereof include sucrose lauric acid ester, sucrose myristic acid ester, sucrose palmitic acid ester, sucrose stearic acid ester, sucrose behenic acid ester, sucrose oleic acid ester, and sucrose erucic acid ester. These may be used alone or in combination.

Of these, sucrose lauric acid ester, sucrose myristic acid ester, sucrose palmitic acid ester, and sucrose stearic acid ester are preferred from the viewpoint of improving absorption in vivo of panaxadiol. Sucrose myristic acid ester and sucrose palmitic acid ester are particularly preferred from the viewpoint of further improving absorption in vivo of panaxadiol.

<<Lecithin>>

Lecithin is one type of phospholipids and also known as phosphatidylcholine. A method for obtaining the lecithin is not particularly limited and may be appropriately selected depending on the intended purpose. For example, the lecithin may be purified from vegetable materials such as soybean, purified from animal-derived materials such as egg yolk, purified from phospholipids, chemically synthesized, enzymatically produced, or a commercial product. The lecithin often contains unsaturated fatty acids, so that the lecithin may be hydrogenated lecithin which has been hardly-oxidized due to hydrogenation to its unsaturated bonds through catalytic reduction. The purified lecithin may further be enzymatically decomposed with phospholipases such as phospholipase A or phospholipase D. These may be used alone or in combination.

Of these, enzymatically decomposed soybean lecithin is preferred from the viewpoint of improving absorption in vivo of panaxadiol.

An amount of at least one of sucrose fatty acid ester and lecithin contained in the panaxadiol-containing composition is not particularly limited and may be appropriately selected depending on the intended purpose. However, a mass ratio of panaxadiol to at least one of sucrose fatty acid ester and lecithin (panaxadiol:at least one of sucrose fatty acid ester and lecithin) is preferably 1:10 to 1:100, more preferably 1:20 to 1:60, particularly preferably 1:40 to 1:45.

Notably, at least one of sucrose fatty acid ester and lecithin is incorporated in the panaxadiol-containing composition for the purpose of further improving absorption in vivo of panaxadiol. However, at least one of sucrose fatty acid ester and lecithin itself has also been known to have cholesterol-reducing effects and arteriosclerosis preventive effects (see International Publication No. WO/97/009059), and thus, advantageous in terms of ingesting for the purposes of controlling blood glucose level or improving glucose metabolism.

<Other Ingredients>

The other ingredients in the panaxadiol-containing composition are not particularly limited and may be appropriately selected depending on the intended purpose. Examples thereof include supplemental materials or additives commonly used for the production of foods or beverages. These may be used alone or in combination of two or more thereof.

The amount of the other ingredients is not particularly limited and may be appropriately selected depending on the intended purpose.

The supplemental materials or additives are not particularly limited and may be appropriately selected depending on the intended purpose. Examples thereof include glucose, fructose, sucrose, maltose, sorbitol, stevioside, rubusoside, corn syrup, lactose, citric acid, tartaric acid, malic acid, succinic acid, lactic acid, L-ascorbic acid, dl-α-tocopherol, sodium erythorbate, glycerin, propylene glycol, gum Arabic, carrageenan, casein, gelatin, pectin, agar, B vitamins, nicotinic-acid amide, calcium pantothenate, amino acids, calcium salts, dyes, perfumes and preservatives.

The amount of the other ingredients contained in the food, beverage or pharmaceutical drug is not particularly limited and may be appropriately selected depending on the intended purpose.

Additionally, the panaxadiol-containing composition may contain a non-ionic surfactant other than the sucrose fatty acid ester. Examples thereof include ester compounds such as sorbitan fatty acid ester, polyoxyethylene sorbitan fatty acid ester, glycerin fatty acid ester, polyglycerin fatty acid ester, polyoxyethylene glycerin fatty acid ester, polyethyleneglycol fatty acid ester; ether compounds such as polyoxyethylene alkylether, and polyoxyethylene polyoxypropylene alkylether; polyoxyethylene castor oil; hydrogenated castor oil, and polyoxyethylene polyoxypropylene polymer.

Also, the panaxadiol-containing composition may be used alone or in combination with another drug containing other active ingredients. The panaxadiol-containing composition also may be incorporated before use into another drug containing other active ingredients.

<Intake>

The intake method, intake amount, intake times, intake period and intake target of the panaxadiol-containing composition are not particularly limited and may be appropriately selected depending on the intended purpose.

The intake method is not particularly limited and may be appropriately selected depending on the intended purpose, but is preferably oral intake, which makes easy and continuous intake possible.

The intake amount is not particularly limited and may be appropriately selected considering various factors of an intake target, such as the age, body weight, constitution, symptom and the presence or absence of administration of a drug containing other active ingredients.

As to the animal species serving as the intake target, the panaxadiol-containing composition is suitably applied to human. However, so long as its effects can be obtained, the panaxadiol-containing composition can be applied to other animals than human, such as mouse, rat, hamster, bird, dog, cat, sheep, goat, bovine, pig and monkey.

<Applications>

The panaxadiol-containing composition can improve absorption in vivo of panaxadiol which has blood glucose level-controlling effects and glucose metabolism-improving effects, therefore, can be suitably used in food or beverage intended for prevention or treatment for diabetes.

In the present invention, "food or beverage" refers to those which are less harmful to human health and which are given orally or through the gastrointestinal tract in the ordinary social life. They are not limited to foods, drugs and quasi drugs within the administrative boundaries, but include a wide variety of orally-given common foods, healthy foods, health-promoting foods, quasi drugs and drugs.

An amount of the panaxadiol-containing composition contained in the food or beverage is not particularly limited and may be appropriately selected depending on the type of the intended food or beverage, as long as it does not impair effects of the present invention. The food or beverage may be the panaxadiol-containing composition itself.

The panaxadiol has bitter taste, so that the panaxadiol-containing composition is preferably in the form of solids such as powder or a tablet from the viewpoint of being easily ingested, in the case where the panaxadiol-containing composition itself is used alone as the food or beverage.

The type of the food or beverage is not particularly limited and may be appropriately selected depending on the intended purpose. Examples thereof include beverages such as refreshing beverages, carbonated beverages, energy beverages, fruit beverages and lactic beverage; frozen desserts such as ice cream, ice sherbet and ice shavings; noodles such as buckwheat noodles, wheat noodles, vermicelli, coats of Chinese dumplings, coats of pork dumplings, Chinese noodles and instant noodles; snacks such as candies, gum, chocolate, tabletted snacks, munches, biscuits, jelly, jam, cream, baked confectionery and bread; marine products such as crab, salmon, Japanese littleneck, tuna, sardine, shrimps, prawns, bonito, mackerel, whale, oyster, saury, squid, bloody clam, scallop, abalone, sea chestnut, salmon caviar and Sulculus diversicolor supertexta; marine/livestock processed foods such as fish minced and steamed, ham and sausage; dairy products such as processed milk and fermented milk; fats and oils or processed foods thereof such as salad oil, Tempura oil, margarine, mayonnaise, shortening, whip cream and dressing; seasonings such as sauce and basting; retort pouch foods such as curry, stew, Oyako-don (a bowl of rice topped with boiled chicken and eggs), rice porridge, Zosui (rice soup), Chuka-don (a bowl of rice with a chop-suey-like mixture on it), Katsu-don (a rice bowl with pork cutlets), Ten-don (a tempura rice bowl), Una-don (an eel rice bowl), hayashi rice (hashed beef with rice), Oden (a dish containing several ingredients such as boiled eggs and radish), mapo doufu, Gyu-don (a beef rice bowl), meat sauce, egg soup, rice omelet, Chinese dumplings, pork dumplings, hamburger steak and meat balls; healthy foods in various forms and dietary supplements; and pharmaceutical drugs and quasi drugs.

EXAMPLES

The present invention will next be described in detail by way of Examples. The present invention should not be construed as being limited to these Examples.

Preparation Example 1

Preparation of Acid-Treated *Panax notoginseng* Product 1 kg of *Panax notoginseng* powder (product of MATSUURA YAKUGYO CO., LTD.) was suspended in 10 L of an aqueous solution containing 5.9% by volume hydrochloric acid and 25% by volume ethanol (2 mol/L hydrochloric acid hydrolyzing liquid). The resultant suspension was allowed to react for 6 hours at 70° C. while slowly stirred. The reaction mixture was cooled on ice and then neutralized with a 5 M aqueous sodium hydroxide solution. The neutralized mixture was 10-fold diluted with distilled water and then filtrated through aspiration. The residue was freeze-dried to prepare an acid-treated *Panax notoginseng* product.

About 0.1 g of the obtained acid-treated *Panax notoginseng* product was accurately weighed, and about 8 mL of ethanol (purity: 99.5% by volume) was added to the sample. The mixture was suspended for 15 min using an ultrasonic bath. The suspension was centrifuged at about 700×g for 10 min, and ethanol (purity: 99.5% by volume) was added to the supernatant so as to have a volume of exactly 10 mL. The thus-prepared liquid was measured through gas chromatography under the following conditions, and the amount of panaxadiol contained therein was found to be 3.5% by mass. Notably, in the following conditions, the retention time of panaxadiol was about 18 min.

[Analysis Conditions]
Gas Chromatograph: GC353B (product of GL Sciences Inc.)
Detector: Flame Ionization Detector (FID)
Injection method: Split injection method (split ratio: 1:50)
Column: DB-17MS (length: 30 m, inner diameter: 0.25 mm, film thickness: 0.25 product of Agilent Technologies, Ltd.)
Column temp.: Initial temp.: 310° C.
  Initial temp. retaining time: 20 min
  Temperature increasing rate: 10° C./min
  Final temp.: 320° C.
  Final temp. retaining time: 14 min
Carrier gas: Helium
Flow rate: 1.5 mL/min
Injection inlet temp.: 320° C.
Detector temp.: 320° C.
Injection amount: 1 µL Comparative Examples 1 and 2

Conventional feed (trade name: CE-2, product of Nosan Corporation) was mixed with the acid-treated *Panax notoginseng* product prepared in Preparation Example 1 in a mixing ratio described in Tables 1-1 or 1-2, and Tables 2-1 or 2-2 to prepare mixed feeds of Comparative Examples 1 and 2, respectively.

Comparative Examples 3 and 4

Conventional feed (trade name: CE-2, product of Nosan Corporation) was mixed with the acid-treated *Panax notoginseng* product prepared in Preparation Example 1 and glycerin monostearate citrate in a mixing ratio described in Tables 1-1 and 2-2 to prepare mixed feeds of Comparative Examples 3 and 4, respectively.

Examples 1 to 10

Conventional feed (trade name: CE-2, product of Nosan Corporation) was mixed with the acid-treated *Panax notoginseng* product prepared in Preparation Example 1 and either sucrose fatty acid ester or lecithin (hereinafter may be referred to as "additive") in a mixing ratio described in Tables 1-1 to 2-2 to prepare mixed feeds of Examples 1 to 10, respectively.

<Evaluation of Absorption In Vivo of Panaxadiol>
—Acclimation of Test Animal—
Rats (Sprague-Dawley rat, male, 6-week-old, product of Japan SLC, Inc.) were acclimated for 5 days with free access to water and conventional feed (trade name: CE-2, product of Nosan Corporation) under the following conditions: environmental temperature of 22±0.5° C., and a light-dark cycle of 12 h of light and 12 h of dark.

—Analysis of Panaxadiol Concentration in Blood—

After acclimation, the rats were bred for 4 days with free access to water and any one of mixed feeds of Examples 1 to 10 and Comparative Examples 1 to 4. After the 4-day breeding, whole blood was taken from the abdominal caudal vena cava of each of rats anesthetized with diethyl ether (product of Wako Pure Chemical Industries, Ltd.). A heparin-treated vacuum blood collection tube (product of NIPRO CORPORATION) was used for separating plasma. Notably, each of the groups in Examples and Comparative Examples contained n=3.

The blood collected from each of the groups was centrifuged at 3,000 rpm for 30 min at room temperature (25±0.5° C.) to thereby separate plasma components. To 3 mL of the plasma components, was added acetonitrile in an amount of 3-fold (V/V) of that of the plasma component, followed by vortexing and centrifuging at 3,500 rpm for 10 min at room temperature (25±0.5° C.). The resultant supernatant was collected into a test tube, followed by evaporating to dryness using a centrifugal evaporator to thereby obtain a solid. To the resultant solid, was added 1 mL of acetonitrile to prepare a sample for high performance liquid chromatography mass spectrometry (LC-MS).

Figure 2:
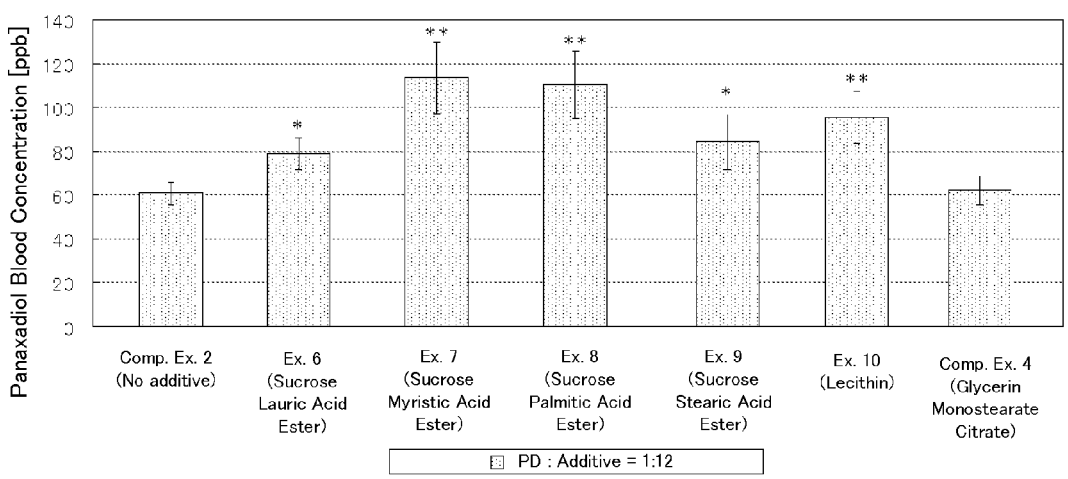
FIG. 2 shows results of PD blood concentrations (ppb) of groups which ingested mixed feeds of Examples 6 to 10 and Comparative Examples 2 and 4.

The sample was analyzed for panaxadiol concentration in blood (ppb) using the following conditions. Tables 1-1 and 1-2, and FIG. 1 show average values of panaxadiol concentrations in blood (PD blood concentrations) of the groups in Examples 1 to 5 and Comparative Examples 1 and 3. Tables 2-1 and 2-2, and FIG. 2 show PD blood concentrations of the groups in Examples 6 to 10 and Comparative Examples 2 and 4.

Notably, Student's t-test was used for statistical calculation, and a two-sided significance level of less than 5% was determined as a significant difference. In Tables 1-1 and 1-2, and FIG. 1, the result of Comparative Example 1 was compared with that of Examples 1 to 5 and Comparative Example 3. In Tables 2-1 and 2-2, and FIG. 2, the result of Comparative Example 2 was compared with that of Examples 6 to 10 and Comparative Example 4. In Tables 1-1 to 2-2 and FIGS. 1 and 2, "*" denotes $p<0.05$ and "**" denotes $p<0.01$.

[LC Analysis Condition]
LC: Waters AQUITY UPLC system (product of Nihon Waters K.K.)
Column: AQUITY UPLC HSS T3 (internal diameter: 2.1 mm, length: 100 mm, particle diameter: 1.7 μm, product of Nihon Waters K.K.)
Mobile phase A: 0.1% by volume formic acid aqueous solution
Mobile phase B: 0.1% by volume formic acid/acetonitrile aqueous solution
Gradient condition:
  Initial concentration: 100% by volume of Mobile phase A
  0 min to 10 min: linear gradient from 100% by volume of Mobile phase
    A to 100% by volume of Mobile phase B
  10 min to 12 min: linear gradient from 100% by volume of Mobile phase
    B to 100% by volume of Mobile phase A
Flow rate: 0.5 mL/min
Column temperature: 40° C.
Injection volume: 5 μL
[MS Analysis Condition]
MS: Waters synapt HDMS system (TOF/MS) (product of Nihon Waters K.K.)
Ionization mode: ESI (+)
Capillary voltage: 3.0 kV
Cone voltage: 20 V
Ion source temperature: 120° C.
Desolvation gas: 350° C., 800 L/hour
Scan time: 1 second
Measurement mass range: m/z=100 to 1,000

—Calculating of Increase Factor of Panaxadiol Concentration in Blood—

Figure 3:
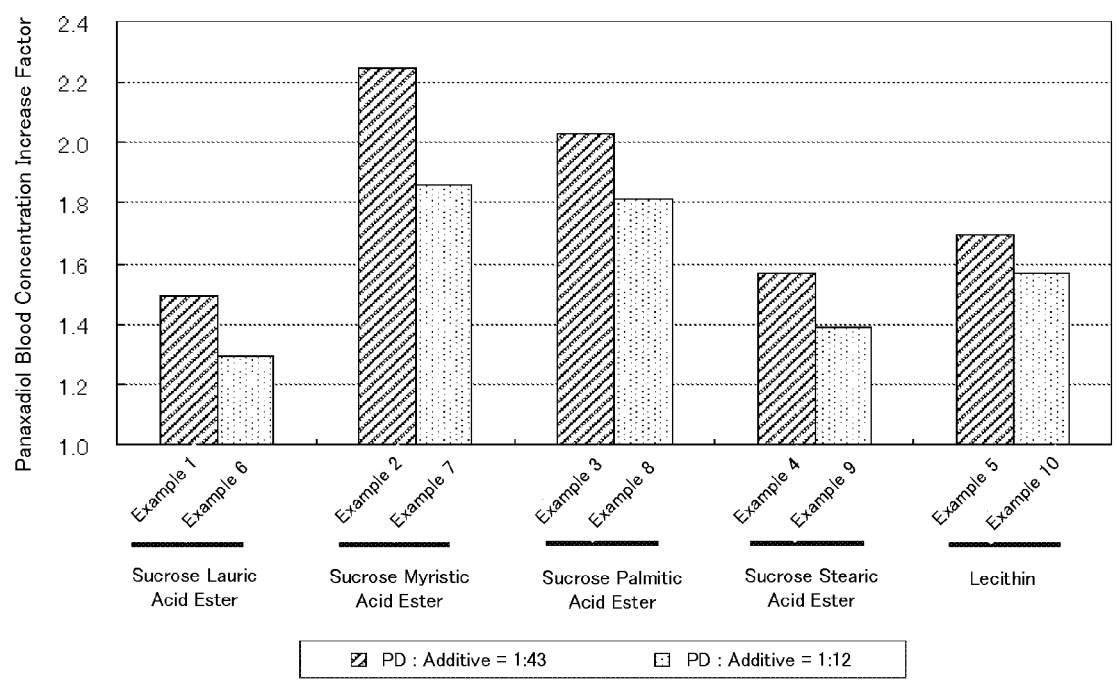
FIG. 3 shows results of increase factors of panaxadiol concentration in blood (PD blood concentration increase factor) in groups which ingested mixed feeds of Examples 1 to 10 when PD blood concentration in a group which ingested a mixed feed of Comparative Example 1 or 2 is assumed to be 1.

Increase factors of panaxadiol concentration in blood (PD blood concentration increase factor) in Examples 1 to 5 and Comparative Example 3 when the PD blood concentration in Comparative Example 1 is assumed to be 1.0; and PD blood concentration increase factors in Examples 6 to 10 and Comparative Example 4 when the PD blood concentration in Comparative Example 2 is assumed to be 1.0 were calculated according to the following Equations. Results are shown in Tables 1-1 to 2-2 and FIG. 3.

Examples 1 to 5 and Comparative Example 3

PD blood concentration increase factor=(PD blood concentration in any one of Examples 1 to 5 and Comparative Example 3)/(PD blood concentration in Comparative Example 1)

Examples 6 to 10 and Comparative Example 4

PD blood concentration increase factor=(PD blood concentration in any one of Examples 6 to 10 and Comparative Example 4)/(PD blood concentration in Comparative Example 2)

TABLE 1-1

| | Component | Comp. Ex. 1 | Ex. 1 | Ex. 2 | Ex. 3 |
|---|---|---|---|---|---|
| | Feed (CE-2) | 98 | 95 | 95 | 95 |
| Acid-Treated *Panax Notoginseng* Product | | 2 | 2 | 2 | 2 |
| Additive | Sucrose Lauric Acid Ester | — | 3 | — | — |
| | Sucrose Myristic Acid Ester | — | — | 3 | — |
| | Sucrose Palmitic Acid Ester | — | — | — | 3 |
| | Sucrose Stearic Acid Ester | — | — | — | — |
| | Lecithin | — | — | — | — |
| Comparative Additive | Glycerin Monostearate Citrate | — | — | — | — |
| | PD:Additive [Mass Ratio] | 1:43 | 1:43 | 1:43 | 1:43 |
| | PD Blood Concentration [ppb] | 36.6 ± 7.9 | 54.6 ± 7.7* | 82.1 ± 18.4* | 74.4 ± 13.3* |
| | PD Blood Concentration Increase Factor | — | 1.5 | 2.2 | 2.0 |

TABLE 1-2

| Component | | Ex. 4 | Ex. 5 | Comp. Ex. 3 |
|---|---|---|---|---|
| Feed (CE-2) | | 95 | 95 | 95 |
| Acid-Treated *Panax Notoginseng* Product | | 2 | 2 | 2 |
| Additive | Sucrose Lauric Acid Ester | — | — | — |
| | Sucrose Myristic Acid Ester | — | — | — |
| | Sucrose Palmitic Acid Ester | — | — | — |
| | Sucrose Stearic Acid Ester | 3 | — | — |
| | Lecithin | — | 3 | — |
| Comparative Additive | Glycerin Monostearate Citrate | — | — | 3 |
| PD:Additive [Mass Ratio] | | 1:43 | 1:43 | 1:43 |
| PD Blood Concentration [ppb] | | 57.3 ± 9.7* | 62.1 ± 9.5* | 38.0 ± 5.0 |
| PD Blood Concentration Increase Factor | | 1.6 | 1.7 | 1.0 | mean ± S.D. (n = 3),
*$p < 0.05$,
**$p < 0.01$, Student's t-test

TABLE 2-1

| Component | | Comp. Ex. 2 | Ex. 6 | Ex. 7 | Ex. 8 |
|---|---|---|---|---|---|
| Feed (CE-2) | | 95 | 95 | 95 | 95 |
| Acid-Treated *Panax Notoginseng* Product | | 3.5 | 3.5 | 3.5 | 3.5 |
| Additive | Sucrose Lauric Acid Ester | — | 1.5 | — | — |
| | Sucrose Myristic Acid Ester | — | — | 1.5 | — |
| | Sucrose Palmitic Acid Ester | — | — | — | 1.5 |
| | Sucrose Stearic Acid Ester | — | — | — | — |
| | Lecithin | — | — | — | — |
| Comparative Additive | Glycerin Monostearate Citrate | — | — | — | — |
| PD:Additive [Mass Ratio] | | 1:12 | 1:12 | 1:12 | 1:12 |
| PD Blood Concentration [ppb] | | 60.9 ± 5.1 | 78.9 ± 7.1* | 113.5 ± 16.2** | 110.4 ± 15.2** |
| PD Blood Concentration Increase Factor | | — | 1.3 | 1.9 | 1.8 |

TABLE 2-2

| Component | | Ex. 9 | Ex. 10 | Comp. Ex. 4 |
|---|---|---|---|---|
| Feed (CE-2) | | 95 | 95 | 95 |
| Acid-Treated *Panax Notoginseng* Product | | 3.5 | 3.5 | 3.5 |
| Additive | Sucrose Lauric Acid Ester | — | — | — |
| | Sucrose Myristic Acid Ester | — | — | — |
| | Sucrose Palmitic Acid Ester | — | — | — |
| | Sucrose Stearic Acid Ester | 1.5 | — | — |
| | Lecithin | — | 1.5 | — |
| Comparative Additive | Glycerin Monostearate Citrate | — | — | 1.5 |
| PD:Additive [Mass Ratio] | | 1:12 | 1:12 | 1:12 |
| PD Blood Concentration [ppb] | | 84.5 ± 12.6* | 95.4 ± 11.8** | 62.2 ± 6.4 |
| PD Blood Concentration Increase Factor | | 1.4 | 1.6 | 1.0 | mean ± S.D. (n = 3),
*$p < 0.05$,
**$p < 0.01$, Student's t-test

From the above results, it has been found that the mixed feeds containing the acid-treated *Panax notoginseng* product in combination with either sucrose fatty acid ester or lecithin more improve absorption of panaxadiol in rats in vivo than the acid-treated *Panax notoginseng* product alone. Especially, it has been found that the mixed feeds containing the acid-treated *Panax notoginseng* product in combination with sucrose myristic acid ester or sucrose palmitic acid ester further improve absorption of panaxadiol in rats in vivo.

The amount of panaxadiol contained in the mixed feed of Comparative Example 2 was 1.75-fold higher than that of Comparative Example 1. Therefore, the PD blood concentration in the Comparative Example 2 was about 1.7-fold higher than that of Comparative Example 1. However, when the PD blood concentrations in Examples 6 to 10 in each of which the mass ratio of panaxadiol to sucrose fatty acid ester or lecithin (panaxadiol additive) was 1:12 were compared with the PD blood concentrations in Examples 1 to 5 in each of which the panaxadiol additive was 1:43, the PD blood concentrations in Examples 6 to 10 were only about 1.4-fold to about 1.5-fold higher than that of Examples 1 to 5. Accordingly, it has been found that the mass ratio of panaxadiol to sucrose fatty acid ester and/or lecithin in the panaxadiol-containing composition is preferably 1:10 to 1:100, more preferably 1:20 to 1:60, particularly preferably 1:40 to 1:45 in terms of absorption efficiency of panaxadiol in blood.

Table 3 shows components used for preparing the mixed feeds of Examples 1 to 10 and Comparative Examples 1 to 4.

TABLE 3

| Component | Number of Carbon Atoms In Fatty Acid | HLB | Trade Name | Supplier |
|---|---|---|---|---|
| Feed | — | — | CE-2 | Nosan Corporation |
| Sucrose Lauric Acid Ester | C12 | 16 | J-1216 | Mitsubishi-Kagaku Foods Corporation |
| Sucrose Myristic Acid Ester | C14 | 16 | J-1416 | Mitsubishi-Kagaku Foods Corporation |
| Sucrose Palmitic Acid Ester | C16 | 16 | J-1616 | Mitsubishi Kagaku Foods Corporation |
| Sucrose Stearic Acid Ester | C18 | 16 | J-1816 | Mitsubishi Kagaku Foods Corporation |
| Lecithin | — | 16 | Sunlecithin A-1 | Taiyo Kagaku Co., Ltd. |
| Glycerin Monostearate Citrate | C17 | 9.5 | 621B | Taiyo Kagaku Co., Ltd. |

Embodiments of the present invention are as follows:
<1> A panaxadiol-containing composition, containing:
   panaxadiol; and
   at least one of sucrose fatty acid ester and lecithin.
<2> The panaxadiol-containing composition according to <1>, wherein the sucrose fatty acid ester is at least one selected from sucrose lauric acid ester, sucrose myristic acid ester, sucrose palmitic acid ester, and sucrose stearic acid ester.
<3> The panaxadiol-containing composition according to <1> or <2>, wherein the lecithin is enzymatically decomposed soybean lecithin.
<4> The panaxadiol-containing composition according to any one of <1> to <3>, wherein the panaxadiol-containing composition is a food or beverage.
<5> The panaxadiol-containing composition according to any one of <1> to <4>, wherein a mass ratio of the panaxadiol to the at least one of sucrose fatty acid ester and lecithin (panaxadiol:at least one of sucrose fatty acid ester and lecithin) is 1:10 to 1:100.

INDUSTRIAL APPLICABILITY

The panaxadiol-containing composition of the present invention can improve absorption in vivo of panaxadiol which has blood glucose level-controlling effects and glucose metabolism-improving effects, therefore, can be suitably used in food or beverage intended for prevention or treatment for diabetes.

The invention claimed is:
1. A panaxadiol-containing composition, comprising:
   panaxadiol; and
   at least one of sucrose fatty acid ester and lecithin;
      wherein the sucrose fatty acid ester is at least one selected from sucrose lauric acid ester, sucrose myristic acid ester, sucrose palmitic acid ester, and sucrose stearic acid ester,
      wherein the lecithin is enzymatically decomposed soybean lecithin, and
      wherein a mass ratio of panaxadiol to at least one of sucrose fatty acid ester and lecithin (panaxadiol:at least one of sucrose fatty acid ester and lecithin) is 1:10 to 1:100.
2. The panaxadiol-containing composition according to claim 1, wherein the panaxadiol-containing composition is a food or beverage.

* * * * *